United States Patent [19]

Stahly et al.

[11] Patent Number: 4,581,463

[45] Date of Patent: Apr. 8, 1986

[54] NUCLEOPHILIC SUBSTITUTION PROCESS COMBINED WITH ADDITIONAL REACTION STEPS

[75] Inventors: G. Patrick Stahly; Barbara C. Stahly, both of Baton Rouge, La.

[73] Assignee: Ethyl Corporation, Richmond, Va.

[21] Appl. No.: 640,004

[22] Filed: Aug. 10, 1984

Related U.S. Application Data

[63] Continuation-in-part of Ser. No. 452,517, Dec. 23, 1982, abandoned, and Ser. No. 452,617, Dec. 23, 1982, abandoned, said Ser. No. 452,517, is a continuation-in-part of Ser. No. 419,341, Sep. 17, 1982, abandoned, which is a continuation-in-part of Ser. No. 312,176, Oct. 16, 1981, abandoned, said Ser. No. 452,617, is a continuation-in-part of Ser. No. 419,344, Sep. 17, 1982, abandoned.

[51] Int. Cl.$^4$ ............... C07D 209/46; C07D 207/18; C07C 79/46
[52] U.S. Cl. ............................ 548/472; 548/565; 560/20; 560/102; 560/47; 560/19; 562/469
[58] Field of Search ............... 560/20; 548/565, 472; 562/469

[56] References Cited

U.S. PATENT DOCUMENTS 3,868,391  2/1975  Carney et al.
4,239,901  12/1980  Rainer ............................ 560/34

OTHER PUBLICATIONS

Golinski et al., Tetrahedron Letters, No. 37 (1978), 3495–3498.
Makosza et al., (I), Jour. Org. Chem., vol. 45 (180), 1534–1535.
House—Modern Synthetic Reactions (1972), 494.
Carney et al., (II), Experientia, vol. 29 (1973), 938.
Makosza (II), Int. Conf. Chem. Biotechnol. Biol. Act. Nat. Prod. (Proc.), 1st (1981), issue 2, 480–490.

Primary Examiner—Bernard Helfin
Attorney, Agent, or Firm—Donald L. Johnson; John F. Sieberth; Patricia J. Hogan

[57] ABSTRACT

Halonitroarylacetic acid esters are prepared by reacting a halonitroaromatic compound with an alpha,alpha-disubstituted acetic acid ester in an inert solvent and in the presence of a base. The halonitroarylacetic acid esters formed by the process can be readily converted into derivatives, such as pharmaceuticals.

16 Claims, No Drawings

4,581,463

NUCLEOPHILIC SUBSTITUTION PROCESS COMBINED WITH ADDITIONAL REACTION STEPS

CROSS-REFERENCE

This application is a continuation-in-part of applications Ser. No. 452,517 and Ser. No. 452,617, both filed Dec. 23, 1982; said application Ser. No. 452,517 being a continuation-in-part of application Ser. No. 419,341, filed Sept. 17, 1982, which in turn is a continuation-in-part of application Ser. No. 312,176, filed Oct. 16, 1981; said application Ser. No. 452,617 being a continuation-in-part of application Ser. No. 419,344, filed Sept. 17, 1982, all of which applications are now abandoned.

FIELD OF INVENTION

This invention relates to halonitroarylacetic acid esters and derivatives thereof, more particularly to processes for preparing the esters and derivatives.

BACKGROUND

It is known that there is a variety of techniques for preparing pharmaceuticals, such as flurbiprofen, indoprofen, pirprofen, and the like. Moreover, as shown by U.S. Pat. No. 3,868,391 (Carney et al. I) and U.S. Pat. No. 4,239,901 (Rainer) and by Carney et al., *Experientia*, Vol. 29, page 938, 1973 (Carney et al. II), it is also known that some of these pharmaceuticals can be prepared via halonitrobenzeneacetic acids and derivatives thereof. A disadvantage of these known techniques of preparing pharmaceuticals and pharmaceutical intermediates has been their being tedious and time-consuming.

Golinski et al., *Tetrahedron Letters*, No. 37, pp. 3495-3498 (1978); Makosza et al., *Journal of Organic Chemistry*, 1980, Vol. 45, pp. 1534-1535; and Makosza, *Int. Conf. Chem. Biotechnol. Biol. Act. Nat. Prod. (Proc.)*, 1st, 1981, Issue 2, pp. 480-490, teach nucleophilic substitution processes wherein nitroaromatic compounds are reacted with various nucleophiles, such as the alpha-halosulfones and N,N-dialkyl-1-haloalkanesulfonamides of Golinski et al., the alpha-substituted acetonitriles of Makosza et al., and the methyl alpha-phenylthioacetate, etc., of Makosza. Makosza, summarizing what he learned from the studies reported in these three articles, teaches on pages 484-485 that (1) a requirement for the operability of a nucleophile in these processes is that it be a CH acid that does not react rapidly with its carbanion—a carbanion having the general structure:

wherein X is a leaving group, Y is a carbanion stabilizing group, and R is H, alkyl, aryl, etc., and in which the three variables must be properly combined and (2) CH acids in which X is halogen generally do not meet this requirement. Makosza et al. show that the operability of such nucleophiles is also dependent on the particular nitroaromatic compound used.

SUMMARY OF INVENTION

An object of this invention is to provide novel processes for preparing halonitroarylacetic acid esters.

Another object is to provide such processes which permit the preparation of the esters in good yield with high selectivity in a very simple and straightforward manner.

A further object is to provide novel, improved processes for preparing derivatives of halonitroarylacetic acid esters.

These and other objects are attained by (A) reacting a halonitroaromatic compound with an alpha,alpha-disubstituted acetic acid ester in an inert solvent and in the presence of a base so as to form a halonitroarylacetic acid ester and (B) when appropriate, converting the halonitroarylacetic acid ester to a desired derivative thereof.

DETAILED DESCRIPTION

Halonitroaromatic compounds utilizable in the practice of the invention include a variety of such compounds—the chief requirements for their utility being that (1) they bear at least one ar-nitro and at least one ar-halo, i.e., fluoro, chloro, bromo, or iodo, substituent, (2) they contain at least one replaceable hydrogen on an aromatic ring to which a nitro group is attached, and (3) they be devoid of substituents which would interfere with the desired nucleophilic substitution reaction.

Thus, the utilizable halonitroaromatic compounds include compounds having one or more simple or fused aromatic rings containing five or six members and either bearing no substituents other than nitro and halo substituents or also bearing any of a variety of inert substituents, i.e., substituents that do not interfere with the desired nucleophilic substitution reaction, such as alkyl, alkoxy, alkylmercapto, trifluoromethyl, dialkylamino, dialkanoylamino, cyano, dialkylcarbamoyl, alkylsulfonyl, dialkylsulfamoyl, alkoxyalkyl, haloalkyl, cycloalkyl, halocycloalkyl, etc.—any alkyl chains in the substituents generally being lower alkyl chains, i.e., alkyl chains containing 1-6 carbons. When the halonitroaromatic compound contains more than one ring, any such inert substituent may be on the same ring as the ring bearing the halo and nitro substituents and/or on a ring which is directly or indirectly attached to the ring bearing the halo and nitro substituents.

When the aromatic ring bearing the halo and nitro substituents is a six-membered ring, there should be at least one replaceable hydrogen in a position para or ortho to the carbon bearing the nitro substituent; and it is preferred that there be a replaceable hydrogen in the para position. Halonitroaromatic compounds having a five-membered ring should have a replaceable hydrogen on a carbon adjacent to, or separated by two ring atoms from, the carbon bearing the nitro substituent.

Exemplary of halonitroaromatic compounds that may be used in the practice of the invention are the 2-, 3-, and 4-chloronitrobenzenes; the 2,3-, 2,4-, 2,5-, 2,6-, 3,4-, and 3,5-dichloronitrobenzenes; the various trichloronitrobenzenes; the corresponding fluoro, bromo, and iodo compounds; the various dimethyl-, diethyl-, and dibutylnitrobenzenes, nitrobiphenyls, benzylnitrobenzenes, nitronaphthalenes, nitro-N,N-diethylanilines, nitrodiphenyl esters, nitro-N-ethylacetanilides, nitrobenzylcyanides, nitrophenyl acetates, nitropyridine-N-oxides, nitroquinolines, nitroisoquinolines, nitrothiophenes, and the like bearing one or more ar-chloro, bromo, fluoro, or iodo substituents and containing at least one replaceable hydrogen in an appropriate position.

Particularly preferred halonitroaromatic compounds are the halonitrobenzenes having a replaceable hydrogen in the position para to the nitro group, and even more preferred are such halonitrobenzenes having a halo substituent in a position ortho to the nitro group. Halonitrobenzenes which are especially preferred are 2-chloronitrobenzene and 2-fluoronitrobenzene, which are readily converted with high selectivity into such products as pirprofen, flurbiprofen, and related anti-inflammatory agents.

The alpha,alpha-disubstituted acetic acid esters that can be used in the practice of the invention also include a variety of such compounds which correspond to the formula:

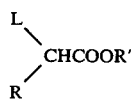

wherein L is a halo, i.e., chloro, bromo, fluoro, or iodo (preferably chloro or bromo) leaving group; R is halo (preferably chloro) or more preferably a hydrocarbyl (e.g., alkyl, alkenyl, alkynyl, cycloalkyl, cycloalkenyl, aryl, aralkyl, etc.) or hydrocarbyloxyhydrocarbyl (e.g. alkoxyalkyl, aryloxyalkyl, alkyoxyaryl, alkoxycycloalkyl, etc.) group which most preferably contains about 1–10 carbons; and R' is a hydrocarbyl group which preferably contains about 1–10 carbons and most preferably is an alkyl group.

A few examples of utilizable alpha,alpha-disubstituted acetic acid esters are alpha-chloropropionates such as methyl, ethyl, propyl, isopropyl, butyl, t-butyl, cyclohexyl, and benzyl 2-chloropropionates; the corresponding alpha-bromopropionates; the corresponding alpha-halobutyrates; and the like. The alpha-haloalpha-hydrocarbylacetic acid esters, i.e., esters of alpha-halo monocarboxylic acids containing at least three carbons, are preferred; and esters of alpha-haloalkanoic acids containing at least three carbons are especially preferred. In another highly desirable embodiment of the invention, the alpha,alpha-disubstituted acetic acid ester is an alpha,alpha-dihaloacetic acid ester, most preferably an alpha,alpha-dichloroacetic acid ester.

The solvent used in the process of the invention may be any solvent that is inert under the conditions of the reaction, i.e., any solvent that will not prevent the reaction from occuring. Such solvents are substantially anhydrous and are generally aprotic, although solvents such as liquid ammonia are also utilizable. Suitable aprotic solvents include, e.g., ethers such as diethyl ether, dibutyl ether, 1-ethoxyhexane, tetrahydrofuran, 1,4-dioxane, 1,3-dioxolane, diglyme, 1,2-diethoxyethane, anisole, etc., and tertiary amines such as pyridine, N-ethylpiperidine, triethyl amine, tributyl amine, N,N-diphenyl-N-methyl amine, N,N-dimethylaniline, etc. However, the preferred aprotic solvents are dipolar aprotic solvents such as dimethyl sulfoxide, N,N-dimethylformamide, N,N-dimethylacetamide, dimethyl sulfone, tetramethylene sulfone, N-methylpyrrolidinone, and the like.

Bases useful in the practice of the invention should be strong bases, e.g., alkaline earth metal compounds such as the oxides and hydrides of calcium, barium, magnesium, and zinc or, more preferably, an alkali metal compound, e.g., an organoalkali metal compound, alkali metal hydride, alkali metal oxide, alkali metal amide, or alkali metal alcoholate, such as butyllithium, phenyllithium, ethylsodium, amylsodium, butylpotassium, benzylpotassium, sodium dimsylate (i.e., the sodium salt of diethylsulfoxide), sodium hydride, potassium hydride, sodium oxide, potassium oxide, sodium amide, potassium amide, lithium diisopropylamide, sodium methoxide, potassium t-butoxide, the sodium salt of the monomethylether of ethylene glycol, sodium phenoxide, and the like. Ordinarily the use of sodium hydride, potassium hydride, sodium t-butoxide, or potassium t-butoxide will be found most convenient and economical.

Use of an alkali metal compound as the base permits the alternatives of using the alkali metal compound alone or in conjunction with a phase transfer catalyst, such as a quaternary ammonium salt, ethylene glycol, or a suitable crown ether. When a phase transfer catalyst is employed, the reaction medium may be any of the aprotic solvents mentioned above, or it may be an inert liquid hydrocarbon such as benzene, toluene, xylene, hexane, heptane, isooctane, or the like.

The halonitroarylacetic acid ester synthesis of the invention appears to occur by a nucleophilic substitution mechanism whereby the ester undergoes a nucleophilic substitution on an unsubstituted ring carbon of the halonitroaromatic compound during which an alpha-substituent of the ester functions as a leaving group. It is conducted in a substantially anhydrous reaction system, and accordingly, the components of the reaction system should be brought together and maintained under a dry inert atmosphere. Thus, while it is possible to conduct the process in the presence of air, it is desirable to maintain the reaction system under an atmosphere of dry nitrogen or the like. The reactants are ordinarily brought together at ambient temperatures, although the temperature may be raised or lowered to suit the needs of the occasion if desired.

The halonitroaromatic compound and alpha,alpha-disubstituted acetic acid ester may be used in amounts such as to provide a stoichiometric excess of either of the reactants or the stoichiometric amount of each. The amount of base employed is preferably such as to provide at least two molar equivalents of base per mole of halonitroaromatic compound, since the use of smaller amounts—although permitting the reaction to occur—makes the base the limiting reagent.

The mode of addition of the ingredients of the reaction system is not particularly critical. Accordingly, it is convenient to add the halonitroaromatic compound to a mixture of the other materials, add the base to a mixture of the other materials, add the reactants to a mixture of the base and inert solvent, introduce all four ingredients simultaneously into the reaction zone, or the like. Since the reaction ordinarily proceeds very rapidly, long reaction times are not required. The reaction will usually be completed within a matter of minutes or a few hours at ambient temperatures.

When derivatives of the halonitroarylacetic acid esters are desired, they may be prepared by employing conventional techniques to convert to the desired derivatives the halonitroarylacetic acid esters made in accordance with the present invention. Thus, for example:

(A) an alkyl 2-(3-chloro-4-nitrobenzene)propionate synthesized by the process of this invention may be hydrogenated to an alkyl 2-(4-aminobenzene)propionate, which in turn may be reacted with phthalic anhydride to form an alkyl 2-(4-phthalimidophenyl)propionate, which may be reduced and hydrolyzed to 2-[4-(1,3-dihydro-1-oxo-2H-isoindol-2-yl)phenyl]propionic acid, i.e., indoprofen, (B) an alkyl 2-(3-chloro-4-nitrobenzene)propionate synthesized by the process of this invention may be hydrolyzed to 2-(3-chloro-4-nitrobenzene)propionic acid, which in turn may be reduced to 2-(4-aminobenzene)propionic acid, reacted with phthalic anhydride to form 2-(4-phthalimidophenyl)propionic acid, and reduced to indoprofen, (C) an alkyl 2-(3-chloro-4-nitrobenzene)propionate synthesized by the process of this invention may be selectively hydrogenated to an alkyl 2-(4-amino-3-chlorobenzene)propionate, which in turn may be reacted with a 1,4-dihalo-2-butene to form an alkyl 2-[3-chloro-4-(pyrrolinyl)phenyl]propionate, which may be hydrolyzed to 2-[3-chloro-4-(3-pyrrolinyl)phenyl]propionic acid, i.e., pirprofen, and (D) an alkyl 2-(3-fluoro-4-nitrobenzene)propionate synthesized by the process of this invention may be hydrogenated to an alkyl 2-(4-amino-3-fluorobenzene)propionate, which in turn may be converted to an alkyl 2-(2-fluoro-4-biphenylyl)propionate—preferably by means of a Gomberg-Bachmann reaction—and subsequently converted to 2-(2-fluoro-4-biphenylyl)propionic acid, i.e., flurbiprofen.

The particular conventional techniques used to convert the halonitroarylacetic acid esters into their various derivatives are not critical, since the overall processes for preparing the derivatives are simplified and made more efficient and economical by the present simplification of the synthesis of the halonitroarylacetic acid esters, regardless of the particular techniques used to convert them into their various derivatives.

As indicated above, the present invention is particularly advantageous in providing a readier and more economical route to the synthesis of flurbiprofen, indoprofen, pirprofen, and other pharmaceuticals that can be prepared from halonitroarylacetic acid esters. Such products include, not only those mentioned above, but a variety of products, such as products disclosed in U.S. Pat. Nos. 3,641,040, 3,657,230, 3,767,805, 3,868,391, 3,936,467, 3,993,763, 3,997,669, 4,010,274, 4,118,504, 4,126,691, 4,163,788, and 4,239,901.

The following examples are given to illustrate the invention and are not intended as a limitation thereof.

EXAMPLE I

A flame-dried flask was purged with nitrogen to provide an inert atmosphere and charged with 2.8 g (58 mmols) of a 50% dispersion of sodium hydride in mineral oil. This was washed with three 10 ml portions of petroleum ether (b.p. 35°-60° C.), dried in a nitrogen stream, slurried in 20 ml of N,N-dimethylformamide (DMF), and cooled in an ice/water bath. A solution of 3.7 g (26 mmols) of 2-fluoronitrobenzene and 3.6 g (29 mmols) of methyl 2-chloropropionate in 5 ml of DMF was added dropwise to the vigorously stirred sodium hydride slurry over a period of 15 minutes. After the addition had been completed, the cooling bath was removed but was reapplied periodically to keep the temperature of the reaction mixture below 30° C. while the mixture was stirred for an additional 30 minutes. The reaction mixture was then poured into 150 ml of cold 1N HCl, and the resulting aqueous mixture was extracted with three 100 ml portions of diethyl ether. The ether layers were combined, dried over MgSO₄, and concentrated to give 7.8 g of an orange oil. Chromatography of this oil on a column of 150 g of 230–400 mesh silica gel afforded 3.1 g of a fraction (eluted with 40% dichloromethane/60% petroleum ether) which contained methyl 2-(3-fluoro-4-nitrobenzene)propionate.

EXAMPLE II

Part A

Into a flask under a nitrogen blanket were placed 6.5 g of sodium hydride (60% in mineral oil, 0.163 mol) and the mineral oil was removed from the sodium hydride with pentane. The resulting dry sodium hydride was slurried in 50 ml of DMF, 0.5 ml of t-butanol was added to the slurry, and the mixture was cooled to 5° C. A solution of 10 g of methyl 2-chloropropionate (0.0816 mol) and 11.5 g of 2-fluoronitrobenzene (0.0816 mol) in 20 ml of DMF was added dropwise to the slurry. After about two-thirds of the reactant solution had been added, a solution of three drops of water in 1 ml of DMF was added to the reaction mixture, and as a result the reaction temperature rose to 25° C. before it could be lowered to 5° C. with an ice bath. After the remainder of the reactant solution was added dropwise, the mixture was allowed to react for 4 hours at room temperature and was poured into cold, dilute HCl. The aqueous mixture was extracted with diethyl ether and the ether extracts were combined, dried, and concentrated to give 18.2 g of an oil. Distillation of this oil at 1 mm afforded a fraction weighing 8 g which contained 92% (GC area %) methyl 2-(3-fluoro-4-nitrobenzene)propionate.

Part B

The material obtained in Part A [8 g of 92% methyl 2-(3-fluoro-4-nitrobenzene)propionate] was dissolved in 60 ml of methanol, and 0.8 g of 5% palladium on carbon was added to the solution. The resulting mixture was hydrogenated in a Parr apparatus (50 psig hydrogen) for 1 hour, filtered, and evaporated to give 6.5 g of material containing 92% (GC area %) methyl 2-(4-amino-3-fluorobenzene)propionate.

Part C

To 50 ml of benzene was added 0.5 g of material obtained in Part B [92% methyl 2-(4-amino-3-fluorobenzene)propionate] and a pinch of silica gel. This solution was brought to a gentle reflux and 0.44 g of isoamyl nitrite was added. After 1 hour at reflux an additional 0.24 g of isoamyl nitrite was added and the mixture was heated at reflux for an additional 30 minutes, after which it was filtered and concentrated to give 0.58 g of material. This material, after purification on two 2 mm silica gel thin layer chromatographic (TLC) plates (eluted with 40% dichloromethane/60% petroleum ether) afforded 0.20 g of methyl 2-(2-fluoro-4-biphenylyl)propionate.

EXAMPLE III

Into a flame-dried flask under nitrogen was placed 0.10 g (2.5 mmols) of a 60% dispersion of sodium hydride in mineral oil. This was washed with 3 ml of petroleum ether (b.p. 35°-60° C.) and slurried in 2.0 ml of 1,4-dimethyl-2-imidazolidinone (DMI). A solution of 0.15 g (1.3 mmols) of methyl 2-chloropropionate and 0.18 g (1.3 mmols) of 3-fluoronitrobenzene in 2.0 ml of DMI was added dropwise to the sodium hydride slurry. The resulting purple mixture was stirred at room temperature for 15 minutes and poured into 20 ml of 10% hydrochloric acid. The aqueous mixture was extracted with three 20 ml portions of diethyl ether, and the ether layers were combined, dried over magnesium sulfate, and concentrated. The residue was purified by preparative TLC to give 0.17 g (60%) of methyl 2-(2-fluoro-4-nitrobenzene)propionate.

EXAMPLE IV

A nitrogen-purged reaction flask was charged with 250 ml of dry DMF. The DMF was cooled to −5° C., and 62.7 g (0.56 mol) of potassium t-butoxide was added. A solution of 40 g (0.28 mol) of 1-fluoro-2-nitrobenzene and 38.7 g (0.28 mol) of ethyl 2-chloropropionate in DMF was added to the cold solution of base over a period of 10 minutes while maintaining the reduced temperature, and this temperature was also maintained while the reaction mixture was stirred for one hour after the addition had been completed. The reaction mixture was then poured into dilute HCl/ice and extracted with portions of ether totaling 700 ml. The combined ether phases are washed, dried, filtered, and evaporated to give 70.2 g of red oil, which was vacuum distilled. A product fraction (50.2 g) boiling at 141°–149° C. at 1 mm of mercury was collected and determined by gas chromatographic (GC) analysis to contain 94 area % ethyl 2-(3-fluoro-4-nitrobenzene)propionate and 6 area % t-butyl 2-(3-fluoro-4-nitrobenzene)propionate.

EXAMPLE V

A flame-dried flask was charged with 3.0 ml (26 mmols) of 2-chloronitrobenzene, 2.9 ml (26 mmols) of methyl 2-chloropropionate, and 25 ml of DMF that had previously been dried over 3-Angstrom molecular sieves. The flask was supported in a water bath, and 1.5 g (31 mmols) of sodium hydride were incrementally added over a period of 20 minutes as a 50% slurry in hydrocarbon oil. Upon the addition of the first incremental portion of the sodium hydride, the reaction mixture became red and thereafter turned deep purple as more of the base was added. After all of the sodium hydride had been charged to the flask, the mixture was stirred at room temperature under a nitrogen atmosphere for 18 hours. The reaction mixture was then poured into 1N HCl and extracted with portions of diethyl ether to form ether layers which were combined, extracted with water, dried over magnesium sulfate, and stripped to give a black oil. An aliquot of the oil was analyzed by means of a gas chromatograph coupled with a mass spectrometer (GC/MS) and found to contain a product having the empirical formula $C_{10}H_{10}ClNO_4$. Another aliquot was subjected to preparative TLC, and NMR analysis of the isolated product was consistent with the compound methyl 2-(3-chloro-4-nitrobenzene)propionate.

EXAMPLE VI

A flame-dried flask was purged with nitrogen to provide an inert atmosphere and charged with 5.1 g (110 mmols) of a 50% dispersion of sodium hydride in hydrocarbon oil. The sodium hydride was washed with 15 ml of petroleum ether (b.p. 35°–60° C.), after which the flask was charged with 15 ml of DMF that had been dried over 3-Angstrom molecular sieves. Then a reaction mixture was formed by the dropwise addition, over 20 minutes, of a solution of 6 ml (51 mmols) of 2-chloronitrobenzene and 6 ml (53 mmols) of methyl 2-chloropropionate in 10 ml of DMF. The mixture turned purple and became hot during the dropwise addition. After completion of this addition, the reaction mixture was stirred for an additional 15 minutes, poured into 200 ml of 1N HCl, and extracted with three 150 ml portions of diethyl ether. The ether layers were combined, dried over magnesium sulfate, and concentrated to give a black oil which was chromatographed on a 200 g silica gel column eluted with 30% methylene chloride/70% petroleum ether. The appropriate fractions were combined and concentrated to afford 8.2 g of material which contained 94% (by GC area percent), i.e., 7.7 g, of methyl 2-(3-chloro-4-nitrobenzene)propionate—a yield of 62%.

EXAMPLE VII

Example VI was repeated except that the 2-chloronitrobenzene/2-chloropropionate/DMF solution was added over a period of 30 minutes during which the temperature of the reaction mixture was maintained at 25°–30° C. by intermittent cooling with an ice/water bath, and stirring of the reaction mixture was continued for 30 minutes after completion of this dropwise addition. The reaction mixture was then poured into 150 ml of 1N HCl and extracted with four 150 ml portions of diethyl ether. The ether layers were combined, dried over $MgSO_4$, and concentrated to give an oil which was adsorbed on 15 g of silica gel (230–400 mesh). This was loaded on a column of 200 g of silica gel which was eluted with 30% dichloromethane/70% petroleum ether under nitrogen pressure to give 0.65 g of unreacted 2-chloronitrobenzene and 8.4 g of methyl 2-(3-chloro-4-nitrobenzene)propionate—a yield of about 68%.

EXAMPLE VIII

Into a flame-dried flask under a blanket of nitrogen were placed 300 mg of a 50% dispersion of sodium hydride in hydrocarbon oil (6.3 mmols) and 5 ml of DMF. The flask was then charged with a solution of 0.56 ml (4.8 mmols) of 2-chloronitrobenzene and 0.65 ml (5.0 mmols) of ethyl 2-bromopropionate in 2 ml of DMF, which was added dropwise over a period of 5 minutes. Upon the addition of the first drop of this solution, the mixture became orange-red in color; and about 5 minutes after the dropwise addition had been completed, the mixture turned deep purple, and a pronounced exotherm was noted. Then a second portion of sodium hydride (4.2 mmols) was added, and another exotherm was observed. A small portion of the reaction mixture was then partitioned between 1N HCl and diethylether. Analysis of the ether layer by GC/MS indicated that ethyl 2-(3-chloro-4-nitrobenzene)propionate had been formed.

EXAMPLE IX

Into a flame-dried flask under nitrogen were placed 50 mg (1.25 mmols) of a 60% dispersion of sodium hydride in mineral oil, which was washed with three 2 ml portions of petroleum ether (b.p. 35°–60° C.) and slurried in 1.0 ml of DMF. Then a solution of 100 mg (0.635 mmol) of 4-chloronitrobenzene and 83 mg (0.677 mmol) of methyl 2-chloropropionate in 1.0 ml of DMF was added dropwise to the slurry, and the resulting purple mixture was stirred for 15 minutes and poured into 20 ml of 1N HCl. The aqueous mixture was extracted with three 20 ml portions of diethyl ether, and the ether layers were combined, dried over $MgSO_4$, concentrated, and placed on a 2 mm silica gel TLC plate. Elution of the plate with 50% petroleum ether/50% dichloromethane afforded 43 mg of 4- chloronitrobenzene and 13 mg of methyl 2-(2-nitro-5-chlorobenzene)propionate.

EXAMPLE X

Into a flame-dried flask under nitrogen were placed 140 mg (1.24 mmols) of potassium t-butoxide, 23 mg (0.064 mmol) of dibenzo 18-crown-6, and 1.0 ml of toluene. While this mixture was vigorously stirred in a room temperature water bath, a solution of 106 mg (0.670 mmol) of 2-chloronitrobenzene and 124 mg (0.633 mmol) of ethyl 2-bromobutyrate in 1.0 ml of toluene was added dropwise. The resulting purple mixture was stirred for 15 minutes and poured into 20 ml of 1N HCl. Then the aqueous mixture was extracted with three 20 ml portions of diethyl ether, and the ether layers were combined, dried over $MgSO_4$, concentrated, and placed on a 2 mm silica gel TLC plate. Elution of the plate with 60% petroleum ether/40% dichloromethane afforded 45 mg of 2-chloronitrobenzene and 27 mg of ethyl 2-(3-chloro-4-nitrobenzene)butyrate.

EXAMPLE XI

A nitrogen-purged, flame-dried flask was charged with 50 mg (1.3 mmols) of a 60% dispersion of sodium hydride in mineral oil. This was washed with three 1 ml portions of petroleum ether (b.p. 35°-60° C.) and slurried in 1.0 ml of DMF. A solution of 80 mg (0.63 mmol) of methyl 2-chloropropionate and 98 mg (0.63 mmol) of 3-chloronitrobenzene in 1.0 ml of DMF was added dropwise to the sodium hydride slurry. The resulting purple mixture was stirred at room temperature for 15 minutes and poured into 20 ml of 10% hydrochloric acid. The aqueous mixture was extracted with three 20 ml portions of diethyl ether, and the ether layers were combined, dried over magnesium sulfate, and concentrated. The residue was purified by preparative TLC to give 13 mg (8.5%) of methyl 2-(2-chloro-4-nitrobenzene)propionate.

EXAMPLE XII

The procedure described in Example XI was repeated using 0.10 g (2.5 mmols) of 60% sodium hydride, 0.15 g (1.3 mmols) of methyl 2-chloropropionate, and 0.31 g (1.3 mmols) of 3-iodonitrobenzene. Analysis of the residue obtained on workup by GC/MS indicated the presence of methyl 2-(2-iodo-4-nitrobenzene)propionate.

EXAMPLE XIII

The procedure described in Example XI was repeated using 0.10 g (2.5 mmols) of 60% sodium hydride, 0.15 g (1.3 mmols) of methyl 2-chloropropionate, and 0.25 g (1.3 mmols) of 3-bromonitrobenzene. The residue obtained on workup was purified by preparative TLC to give 15 mg (8.3%) of methyl 2-(2-bromo-4-nitrobenzene)propionate.

EXAMPLE XIV

The procedure described in Example XI was repeated using 0.10 g (2.5 mmols) of 60% sodium hydride, 0.15 g (1.3 mmols) of methyl 2-chloropropionate, and 0.24 g (1.3 mmols) of 2,3-dichloronitrobenzene. The residue obtained on workup was purified by preparative TLC to give 37 mg (11%) of methyl 2-(2,3-dichloro-4-nitrobenzene)propionate.

EXAMPLE XV

The procedure described in Example XI was repeated using 0.10 g (2.5 mmols) of 60% sodium hydride, 0.15 g (1.3 mmols) of methyl 2-chloropropionate, and 0.25 g (1.3 mmols) of 4-bromonitrobenzene. The residue obtained on workup was purified by preparative TLC to give 40 mg (7%) of methyl 2-(5-bromo-2-nitrobenzene)propionate.

EXAMPLE XVI

A mixture of 1.0 g (3.7 mmols) of methyl 2-(3-chloro-4-nitrobenzene)propionate (91% pure by GC), 0.37 g (4.5 mmols) of anhydrous sodium acetate, and 0.1 g of 7% palladium on carbon in 15 ml of methanol was hydrogenated in an agitated vessel at 50 psig for 16 hours. The mixture was then filtered, and the catalyst was washed with two 5 ml portions of methanol. The filtrate was concentrated under vacuum, and the residue was partitioned between 20 ml of dichloromethane and 20 ml of saturated sodium bicarbonate solution. The organic layer was dried over $MgSO_4$ and concentrated to give 0.66 g of an oil which, by GC, contained 89% methyl 2-(4-aminobenzene)propionate.

The preceding examples demonstrate the utility of the invention in the preparation of halonitroarylacetic acid esters. The following two examples show that similar results are not achieved when the alpha,alpha-disubstituted acetic acid esters of the invention are replaced with other compounds having an acidity close to or greater than the acidity of those alpha,alpha-disubstituted acetic acid esters, thus demonstrating that it is not the degree of acidity of the nucleophile that determines its operability.

COMPARATIVE EXAMPLE A

Into a flame-dried flask under nitrogen were placed 50 mg of a 60% dispersion of sodium hydride in mineral oil. This was washed with three 2 ml portions of petroleum ether (b.p. 35°-60° C.) and slurried in 1 ml of DMF. A solution of 0.055 ml of methyl chloroacetate and 0.070 ml of 2-chloronitrobenzene in 1 ml of DMF was added dropwise to the sodium hydride slurry. After the resulting mixture was allowed to react for 15 minutes, a portion of it was partitioned between 1N HCl and diethyl ether. GC and TLC analyses of the ether layer indicated the absence of any substitution product.

COMPARATIVE EXAMPLE B

Comparative Example A was repeated except that the 0.055 ml of methyl chloroacetate was replaced with 0.065 ml of 1-chloro-1-nitropropane. Again it was found that GC and TLC analyses of the ether layer indicated the absence of any substitution product.

It is obvious that many variations can be made in the products and processes set forth above without departing from the spirit and scope of this invention.

We claim:

1. A process which comprises (A) reacting a fluoronitrobenzene with an alpha-haloalkanoate containing at least three carbons in the acid moiety in a substantially anhydrous dipolar aprotic solvent and in the presence of an alkali metal compound so as to form a 2-(fluoronitrobenzene)alkanoate, (B) reducing the 2-(fluoronitrobenzene)alkanoate to a 2-(aminofluorobenzene)alkanoate, (C) converting the 2-(aminofluorobenzene)alkanoate to a 2-(fluorobiphenylyl)alkanoate by replacing the amino group with an aryl group, and (D) hydrolyzing the 2-(fluorobiphenylyl)alkanoate to the corresponding 2-(fluorobiphenylyl)alkanoic acid.

2. The process of claim 1 wherein the fluoronitrobenzene is 2-fluoronitrobenzene, the alpha-haloalkanoate is an alkyl alpha-chloro- or alpha-bromopropionate, the solvent is N,N-dimethylformamide, and the alkali metal compound is a hydride or alcoholate of sodium or potassium.

3. A process which comprises (A) reacting a halonitrobenzene with an alpha-haloalkanoate containing at least three carbons in the acid moiety in a substantially anhydrous dipolar aprotic solvent and in the presence of an alkali metal compound so as to form a 2-(halonitrobenzene)alkanoate, (B) reducing the 2-(halonitrobenzene)alkanoate to a 2-(aminohalobenzene)alkanoate, (C) reacting the 2-(aminohalobenzene)alkanoate with a 1,4-dihalo-2-butene to form a 2-[halo-(3-pyrrolinyl)phenyl]alkanoate, and (D) hydrolyzing the 2-[halo-(3-pyrrolinyl)phenyl]alkanoate to a 2-[halo-(3-pyrrolinyl)phenyl]alkanoic acid.

4. The process of claim 3 wherein the halonitrobenzene is 2-chloronitrobenzene, the alpha-haloalkanoate is an alkyl alpha-chloro- or alpha-bromopropionate, the solvent is N,N-dimethylformamide, and the alkali metal compound is a hydride or alcoholate of sodium or potassium.

5. A process which comprises (A) reacting a halonitrobenzene with an alpha-haloalkanoate containing at least three carbons in the acid moiety in a substantially anhydrous dipolar aprotic solvent and in the presence of an alkali metal compound so as to form a 2-(halonitrobenzene)alkanoate, (B) hydrogenating the 2-(halonitrobenzene)alkanoate to form a 2-(aminobenzene)alkanoate, (C) reacting the 2-(aminobenzene)alkanoate with phthalic ahydride to form a 2-(phthalimidophenyl)alkanoate, and (D) reducing and hydrolyzing the 2-(phthalimidophenyl)alkanoate to form a 2-(1,3-dihydro-1-oxo-2H-isoindol-2-ylphenyl)alkanoic acid.

6. The process of claim 5 wherein the halonitrobenzene is 2-(chloronitrobenzene, the alpha-haloalkanoate is an alkyl alpha-chloro- or alpha-bromopropionate, the solvent is N,N-dimethylformamide, and the alkali metal compound is a hydride or alcoholate of sodium or potassium.

7. A process which comprises (A) reacting a halonitrobenzene with an alpha-haloalkanoate containing at least three carbons in the acid moiety in a substantially anhydrous dipolar aprotic solvent and in the presence of an alkali metal compound so as to form a 2-(halonitrobenzene)alkanoate, (B) hydrolyzing the 2-(halonitrobenzene)alkanoate to a 2-(halonitrobenzene)alkanoic acid, (C) reducing the 2-(halonitrobenzene)alkanoic acid to a 2-(aminobenzene)alkanoic acid, (D) reacting the 2-(aminobenzene)alkanoic acid with phthalic anhydride to form a 2-(phthalimidophenyl)alkanoic acid, and (E) reducing the 2-(phthalimidophenyl)alkanoic acid to a 2-(1,3-dihydro-1-oxo-2H-isoindol-2-ylphenyl)alkanoic acid.

8. The process of claim 7 wherein the halonitrobenzene is 2-chloronitrobenzene, the alpha-haloalkanoate is an alkyl alpha-chloro- or alpha-bromopropionate, the solvent is N,N-dimethylformamide, and the alkali metal compound is a hydride or alcoholate of sodium or potassium.

9. The process of claim 1 wherein the fluoronitrobenzene is 2-fluoronitrobenzene.

10. The process of claim 1 wherein the alpha-haloalkanoate is an alkyl alpha-chloro- or alpha-bromopropionate.

11. The process of claim 1 wherein the alkali metal compound is a hydride or alcoholate of sodium or potassium.

12. The process of claim 1 wherein the solvent is N,N-dimethylformamide.

13. The process of claim 3 wherein the halonitrobenzene is 2-chloronitrobenzene.

14. The process of claim 3 wherein the alpha-haloalkanoate is an alkyl alpha-chloro- or alpha-bromopropionate.

15. The process of claim 3 wherein the alkali metal compound is a hydride or alcoholate of sodium or potassium.

16. The process of claim 3 wherein the solvent is N,N-dimethylformamide.

* * * * *